US009693769B2

(12) United States Patent
Takahashi et al.

(10) Patent No.: US 9,693,769 B2
(45) Date of Patent: Jul. 4, 2017

(54) SUTURE DEVICE

(71) Applicant: OLYMPUS CORPORATION, Tokyo (JP)

(72) Inventors: Shinji Takahashi, Tokyo (JP); Tatsutoshi Hashimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/918,897

(22) Filed: Oct. 21, 2015

(65) Prior Publication Data

US 2016/0038140 A1 Feb. 11, 2016

Related U.S. Application Data

(63) Continuation of application No. PCT/JP2014/068337, filed on Jul. 9, 2014.

(Continued)

(51) Int. Cl.
*A61B 17/04* (2006.01)
*A61B 17/062* (2006.01)
(Continued)

(52) U.S. Cl.
CPC ...... *A61B 17/0483* (2013.01); *A61B 17/0469* (2013.01); *A61B 17/0625* (2013.01);
(Continued)

(58) Field of Classification Search
CPC ............ A61B 17/0483; A61B 17/0469; A61B 17/0625; A61B 17/0474
See application file for complete search history.

(56) References Cited

U.S. PATENT DOCUMENTS 5,364,409 A 11/1994 Kuwabara et al.
5,480,406 A 1/1996 Nolan et al.
(Continued)

FOREIGN PATENT DOCUMENTS

EP 2 255 733 A1 12/2010
JP H05-88507 U 12/1993
(Continued)

OTHER PUBLICATIONS

Aug. 26, 2014 International Search Report issued in International Patent Application No. PCT/JP2014/068337.
(Continued)

*Primary Examiner* — Anh Dang
(74) *Attorney, Agent, or Firm* — Oliff PLC

(57) ABSTRACT

A suture device includes: a longitudinal member extended along a longitudinal axis; a first grasping member and a second grasping member provided at a distal portion of the longitudinal member and configured to enable opening-closing movement; an opening-closing mechanism configured to open and close the first grasping member and the second grasping member; a delivery mechanism configured to deliver a distal member between the first grasping member and the second grasping member, the distal member to which a suture thread is fixed; and an engage portion supported by one of the first grasping member and the second grasping member so as to protrude from a distal end of at least one of the first grasping member and the second grasping member and having an engaging-surface capable of engaging the suture thread.

6 Claims, 18 Drawing Sheets

Related U.S. Application Data

(60) Provisional application No. 61/862,684, filed on Aug. 6, 2013.

(51) Int. Cl.
 *A61B 17/00* (2006.01)
 *A61B 17/06* (2006.01)

(52) U.S. Cl.
 CPC .......... *A61B 2017/0034* (2013.01); *A61B 2017/0417* (2013.01); *A61B 2017/0474* (2013.01); *A61B 2017/06033* (2013.01)

(56) References Cited

U.S. PATENT DOCUMENTS

| | | | |
|---|---|---|---|
| 5,709,694 A | 1/1998 | Greenberg et al. | |
| 5,792,177 A | 8/1998 | Kaseda | |
| 7,112,208 B2* | 9/2006 | Morris | A61B 17/0469 |
| | | | 606/144 |
| 2003/0105474 A1* | 6/2003 | Bonutti | A61B 17/04 |
| | | | 606/139 |
| 2003/0220658 A1 | 11/2003 | Hatch et al. | |
| 2004/0260314 A1* | 12/2004 | Lizardi | A61B 17/0469 |
| | | | 606/144 |
| 2011/0040308 A1 | 2/2011 | Cabrera et al. | |
| 2013/0072948 A1* | 3/2013 | States, III | A61B 17/0483 |
| | | | 606/145 |

FOREIGN PATENT DOCUMENTS

| | | |
|---|---|---|
| JP | H09-266911 A | 10/1997 |
| JP | 2001-500765 A | 1/2001 |
| JP | 2009-279395 A | 12/2009 |
| WO | 98/11829 A1 | 3/1998 |

OTHER PUBLICATIONS

Mar. 8, 2017 European Search Report issued in Application No. 14835431.9.

* cited by examiner

SUTURE DEVICE

The present application is a Continuation of International Patent Application No. PCT/JP2014/068337, filed Jul. 9, 2014, claiming priority on U.S. Provisional Application No. 61/862,684, filed on Aug. 6, 2013, said US Patent Provisional Applications and said PCT Application being incorporated herein by reference.

BACKGROUND OF INVENTION

Field of the Invention

The present invention relates to a medical suture device.

Description of Related Art

Conventionally, a suture device is known that can perform a suture procedure in a body. Using such a device and an endoscope, a continuous suture can be made by repeatedly piercing a needle into a tissue numerous times to sew tissue without removing the suture device from the body.

For a continuous suture, a suture device described in Japanese Unexamined Patent Application, First Publication No. 2009-279395 and a suture needle (distal member) to which a suture thread is fixed are used. The suture device described in Japanese Unexamined Patent Application, First Publication No. 2009-279395 includes a body portion having an elongated tubular member (longitudinal member), and the tubular member extends from the body portion to a distal side. A first jaw (first grasping member) and a second jaw (second grasping member) are movably mounted on a distal end of the tubular member. Both of the jaws can be operated between an opened position at which they are substantially spaced at an interval and a closed position at which they substantially come into contact with each other. Both of the jaws are provided to pass the suture needle through the tissue by being alternately engaged with the suture needle. In particular, both of the jaws of Japanese Unexamined Patent Application, First Publication No. 2009-279395 include needle holes for receiving the suture needle. A toggle lever is provided on the body portion, and is operated to alternately fix the suture needle in the needle hole of each jaw. The suture needle is formed with a slot. The jaws are alternately engaged with the slot, thereby fixing the suture needle.

As the toggle lever of the suture device having such configuration is manipulated, edges of an opening in the tissue are sewn along the opening in turn. Thereby, continuous suture of the tissue can be performed.

After both of the edges of the tissue are sewn, it is necessary to form a knot at the suture thread to hold a state of suturing the tissue. It is described in U.S. Pat. No. 5,480,406 that grasping forceps are introduced into a body from an opening different from an opening for introducing a suture device into the body. Thus, a knot is formed at the suture thread by the suture device and the grasping forceps.

SUMMARY OF THE INVENTION

According to a first aspect of the present invention, a suture device includes: a longitudinal member extended along a longitudinal axis; a first grasping member and a second grasping member provided at a distal portion of the longitudinal member and configured to enable opening-closing movement; an opening-closing mechanism configured to open and close the first grasping member and the second grasping member; a delivery mechanism configured to deliver a distal member between the first grasping member and the second grasping member, the distal member to which a suture thread is fixed; and an engage portion supported by one of the first grasping member and the second grasping member so as to protrude from a distal end of at least one of the first grasping member and the second grasping member and having an engaging-surface capable of engaging the suture thread According to a second aspect of the present invention, in the suture device according the first aspect, the engage portion may be provided to be movable between a distal side position located at a distal side relative to a receiving portion which is provided for the second grasping member, and on which the distal member is detachably mounted and a proximal side position located at a proximal side relative to the receiving portion According to a third aspect of the present invention, in the suture device according the second aspect, the distal side position may be located at a distal side relative to the first grasping member and second grasping member.

According to a fourth aspect of the present invention, in the suture device according the first aspect, the suture device may further include: a rod-like member configured to extend along the longitudinal axis and provided at the second grasping member so as to be movable; and a support member configured to hold the rod-like member to be movable along a longitudinal axis of the second grasping member. A distal portion of the rod-like member may be connected to the engage portion.

According to a fifth aspect of the present invention, in the suture device according the first aspect, the distal member may be a suture needle. The suture device may further comprise a needle-fixing member being inserted into the second grasping member and configured to fix the suture needle to the second grasping member. The needle-fixing member may have a distal portion protruding from a distal end of the second grasping member; and the engage portion may be provided at the distal portion of the needle-fixing member.

According to a sixth aspect of the present invention, in the suture device according the first aspect, the first grasping member may have a first surface facing the second grasping member; the second grasping member may have a second surface facing the first grasping member; the engage portion may be supported by the second grasping member; and the engaging-surface may extend in a direction approximately perpendicular to the first surface, and from the first surface toward the second surface.

According to a seventh aspect of the present invention, in the suture device according the sixth aspect, the engage portion may be configured to be movable along the longitudinal axis between a distal side and a proximal side relative to the distal member.

DETAILED DESCRIPTION OF THE INVENTION

First Embodiment

Hereinafter, a suture system in which a first embodiment of a suture device according to the present invention is used will be described with reference to FIGS. 1 to 16.

Figure 1:
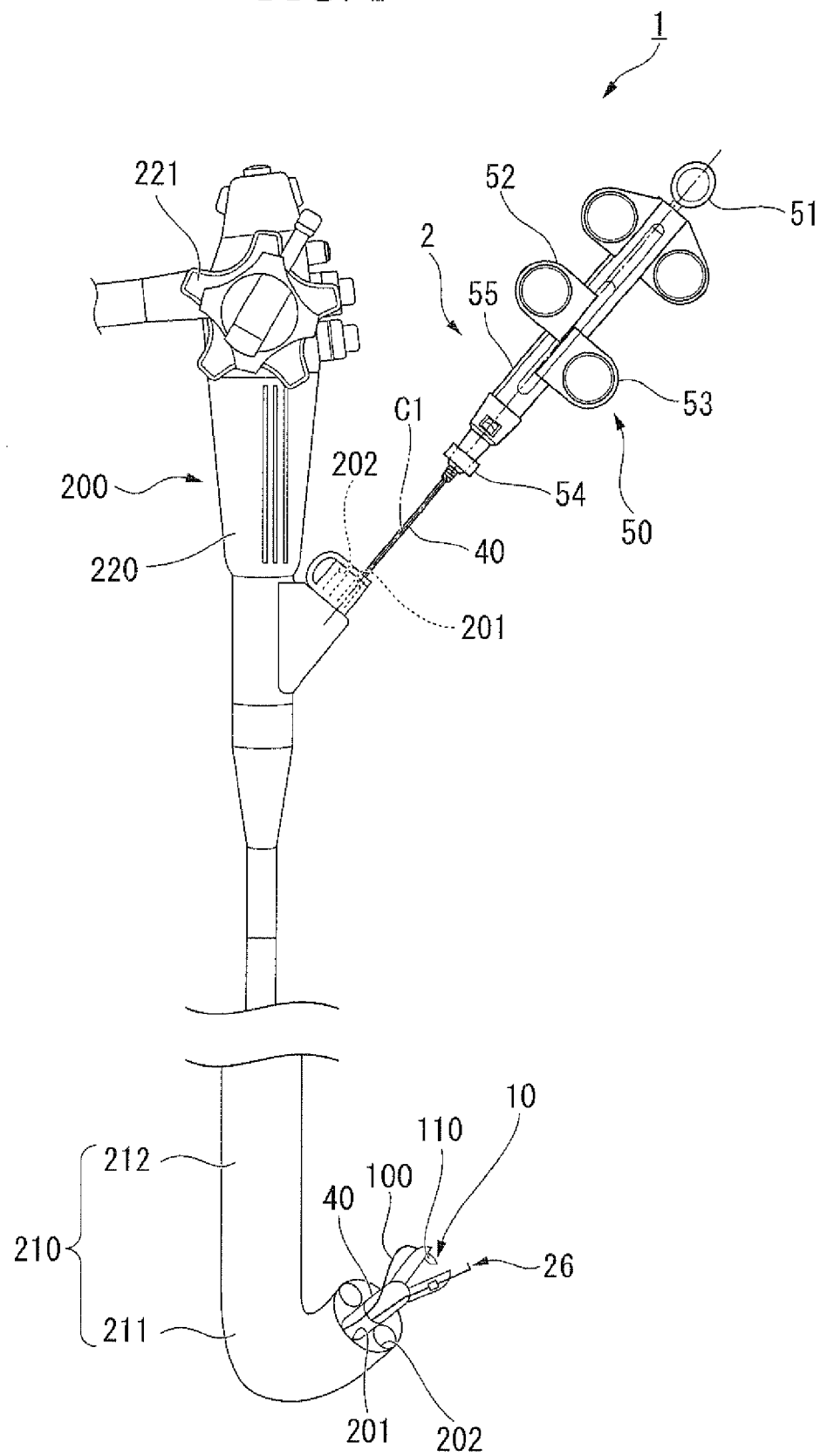
FIG. 1 is an overall view of a suture system provided with a suture device according to a first embodiment of the present invention.

As illustrated in FIG. 1, a suture system 1 is a system that sews tissue using a suture needle (distal member) 110 to which a suture thread 100 is fixed. This suture system 1 is provided with an endoscope 200, and a suture device 2 for puncturing the tissue with the suture needle 110.

Figure 2:
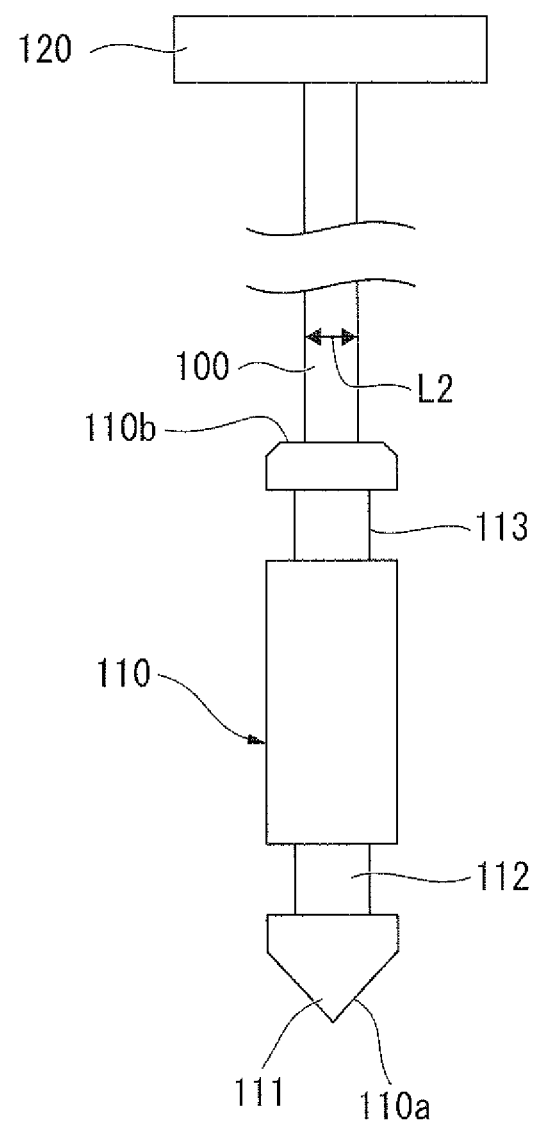
FIG. 2 is a schematic view of a suture needle used in the suture device according to the first embodiment of the present invention.

As illustrated in FIG. 2, the suture needle 110 is formed in a columnar shape, and has a cutting portion 111 sharply formed at a first end 100a thereof in a conical shape. Recesses 112 and 113 that are recessed from an outer circumferential surface are formed in the whole outer circumference of sides of the first and second ends 110a and 110b of the suture needle 110.

A distal end of the suture thread 100 is fixed to the second end 110b of the suture needle 110 by, for instance, an adhesive. A T-bar 120 having a larger outer diameter than the suture thread 100 is fixed to a proximal end of the suture thread 100.

As illustrated in FIG. 1, the suture device 2 has a treatment section 10, a longitudinal member 40, and a manipulation section 50. The longitudinal member 40 runs along a longitudinal axis C1, and the treatment section 10 is provided at a distal portion of the longitudinal member 40. The manipulation member 50 is provided at a proximal portion of the longitudinal member 40.

Figure 3:
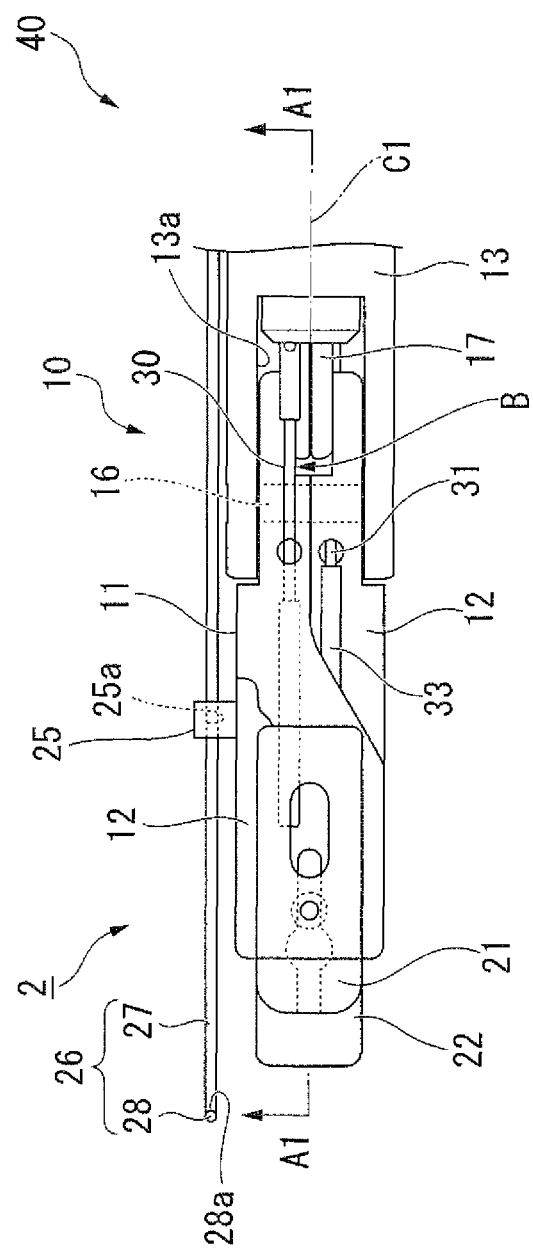
FIG. 3 is a plan view cutting away a part of a treatment section of the suture device according to the first embodiment of the present invention.
Figure 4:
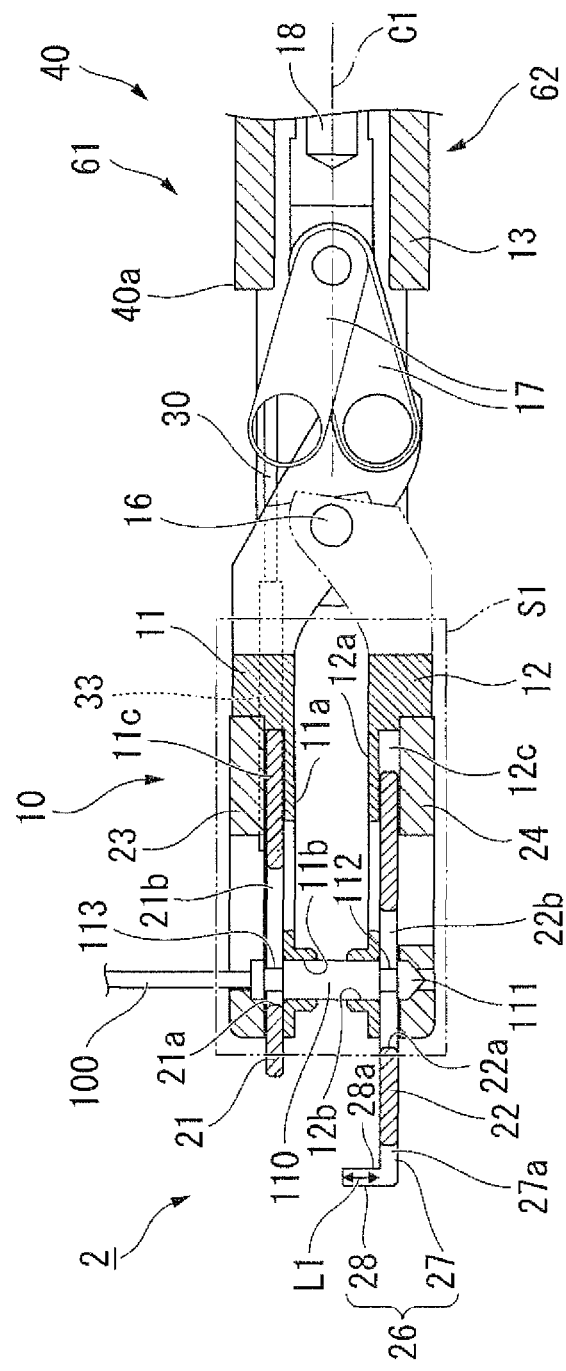
FIG. 4 is a sectional view taken along line A1-A1 of FIG. 3.
Figure 5:
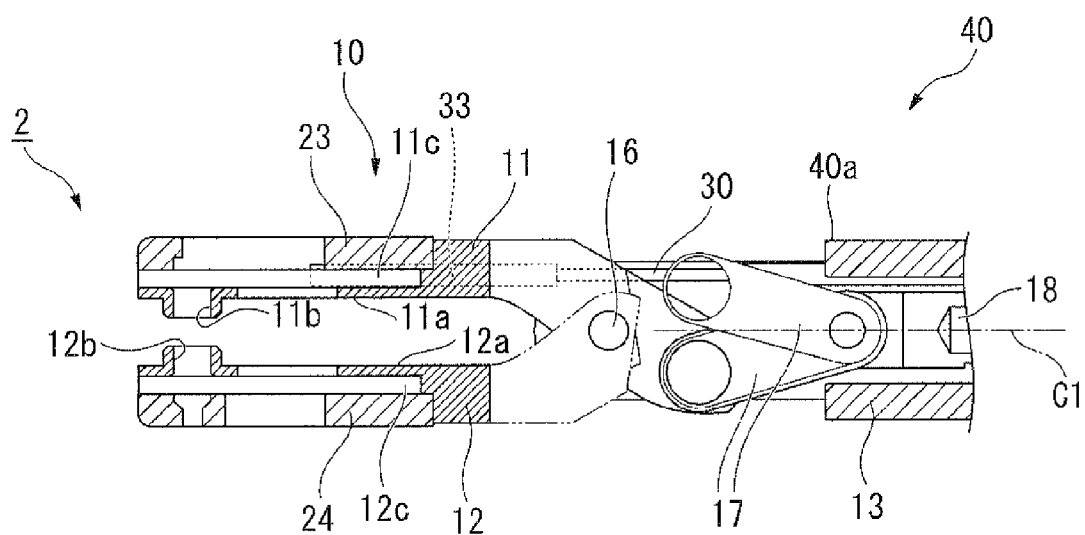
FIG. 5 is a sectional view illustrating a state in which a suture needle and a needle-fixing member are not attached in FIG. 4.

As illustrated in FIGS. 3 to 5, the treatment section 10 has a first grasping member 11, a second grasping member 12, and a cover member 13. The first grasping member 11 and the second grasping member 12 can be opened and closed to deliver the suture needle 110. The cover member 13 connects the grasping members 11 and 12 and the longitudinal member 40. A hook 26 to be described below is not illustrated in FIG. 5.

The grasping members 11 and 12 are relatively rotatably connected at proximal portions thereof by a pin 16. Distal portions of the grasping members 11 and 12 allow opening and closing movements in which the grasping members 11 and 12 are moved away from each other and are moved to close with each other by rotating about a central axis of the pin 16 and opened in directions away from each other and a movement in which they are rotated about the central axis of the pin 16 and closed in directions toward each other.

The first grasping member 11 and the second grasping member 12 have opposed surfaces 11a and 12a that are faced to each other. The opposed surfaces 11a and 12a are nearly parallel when the suture needle 110 is attached to one of the grasping members 11 and 12 and the grasping members 11 and 12 are completely closed.

A hollow 11b is formed in the opposed surface 11a. The hollow 11b is hollowed in a direction perpendicular to the opposed surface 11a in order to support the suture needle 110. A hollow (receiving portion) 12b is formed in the opposed surface 12a. The hollow 12b is hollowed in a direction perpendicular to the opposed surface 12a in order to support the suture needle 110.

The hollow 11b formed in the first grasping member 11 has a shape following a shape of the second end 110b of the suture needle 110. The hollow 12b formed in the second grasping member 12 has a shape following a shape of the cutting portion 111 of the first end 110a of the suture needle 110. That is, the second end 110b of the suture needle 110 is fitted into the hollow 11b, and the first end 110a of the suture needle 110 is fitted into the hollow 12b. Thereby, the suture needle 110 is detachably attached to the grasping members 11 and 12.

Links 17 are connected to proximal ends of the grasping members 11 and 12, respectively. Further, a distal portion of an opening-closing wire 18 is fixed to the links 17.

The links 17 are provided to convert advancing and retreating movements of the opening-closing wire 18 into the opening and closing movements of the grasping members 11 and 12. A distal portion of the opening-closing wire 18 is connected to the grasping members 11 and 12 via the links 17. A proximal end of the opening-closing wire 18 is disposed at the manipulation section 50 (see FIG. 1). The opening-closing wire 18 is a wire (e.g., a stranded wire) fixed to proximal ends of the links 17, and is inserted into a coil sheath 42 (see FIG. 9) inside the longitudinal member 40.

As illustrated in FIG. 4, a first needle-fixing member 21 is disposed inside the first grasping member 11, and the second needle-fixing member 22 is disposed inside the second grasping member 12. To be specific, as illustrated in FIG. 5, the grasping members 11 and 12 are provided with accommodating portions 11c and 12c and lids 23 and 24. As illustrated in FIG. 4, the accommodating portions 11c and 12c are formed in groove shapes, and the needle-fixing members 21 and 22 are inserted in the accommodating portions 11c and 12c. The lids 23 and 24 cover the respective accommodating portions 11c and 12c.

Grooves extending from the distal ends toward the proximal ends of the grasping members 11 and 12 are formed in the accommodating portions 11c and 12c. The distal ends of the accommodating portions 11c and 12c are open.

The first needle-fixing member 21 formed in a plate shape is inserted into the accommodating portion 11c.

Figure 6:
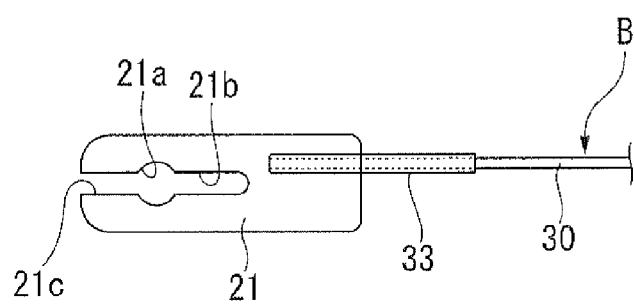
FIG. 6 is a plan view illustrating a constitution of a part of the treatment section in the first embodiment of the present invention.

As illustrated in FIG. 6, a through-hole 21a, a communication-hole 21b, and a slit 21c are formed in the first needle-fixing member 21. As illustrated in FIGS. 4 and 6, the through-hole 21a is bored in a thickness direction of the first grasping member 11. The communication-hole 21b is formed from the through-hole 21a toward the proximal end and is connected to the through-hole 21a. The slit 21c is connected to the through-hole 21a, and is formed to extend from the through-hole 21a toward the distal end.

The through-hole 21a has approximately the same inner diameter as the hollow 11b (see FIGS. 4 and 5) formed in the first grasping member 11. The second end 110b of the suture needle 110 can be inserted into the through-hole 21a.

A width of the communication-hole 21b is smaller than the inner diameter of the through-hole 21a, is greater than an outer diameter of the recess 113 formed in the suture needle 110, and is smaller than an outer diameter of the suture needle 110. A width of the slit 21c is greater than the outer diameter of the suture thread 100. Thereby, when the recess 113 of the suture needle 110 is inserted into the communication-hole 21b, the second end 110b of the suture needle 110 is fixed to the first needle-fixing member 21. The suture thread 100 can pass through the slit 21c. As illustrated in FIG. 4, the second needle-fixing member 22 formed in a plate shape is inserted in the accommodating portion 12c.

A through-hole 22a and a communication-hole 22b that are similar to the through-hole 21a and the communication-hole 21b of the second needle-fixing portion 21 are formed in the second needle-fixing member 22. When the recess 112 of the suture needle 110 is inserted into the communication-hole 22b, the first end 110a of the suture needle 110 is fixed to the second needle-fixing member 22.

As illustrated in FIG. 3, a tubular support member 25 is fixed to the second grasping member 12. A tube hole 25a of the support member 25 extends along the second grasping member 12 nearly in parallel to the longitudinal axis C1. A rod-like member 27 of the hook 26 is inserted through the tube hole 25a of the support member 25. That is, the support member 25 holds the rod-like member 27 to be movable along a longitudinal axis of the second grasping member 12.

An engage portion 28 is provided at least one of the first grasping member 11 and the second grasping member 12. The engage portion 28 can engage the suture thread 100. In the present embodiment, as illustrated in FIGS. 3 and 4, the engage portion 28 formed in a rod shape is connected to a distal portion 27a of the rod-like member 27. As illustrated in FIG. 4, the engage portion 28 extends approximately perpendicular to the opposed surface 12a in a direction approximately orthogonal to the rod-like member 27, i.e., in a direction directed from the opposed surface 12a toward the opposed surface 11a. An engaging-surface 28a provided at a proximal side of the engage portion 28 is directed to a proximal side. The suture thread 100 to be described below can be engaged with the engaging-surface 28a. A length L1 of the engaging-surface 28a in a longitudinal direction of the engage portion 28 is equal to or greater than an outer diameter L2 of the suture thread 100 (see FIG. 2).

The hook 26 is formed by bending a wire such as a stainless steel wire at a portion at which the rod-like member 27 and the engage portion 28 are connected.

The rod-like member 27 advances or retreats in the tube hole 25a of the support member 25, and thereby the hook 26 can move along the longitudinal axis C1 relative to the support member 25 or the second grasping member 12.

Figure 7:
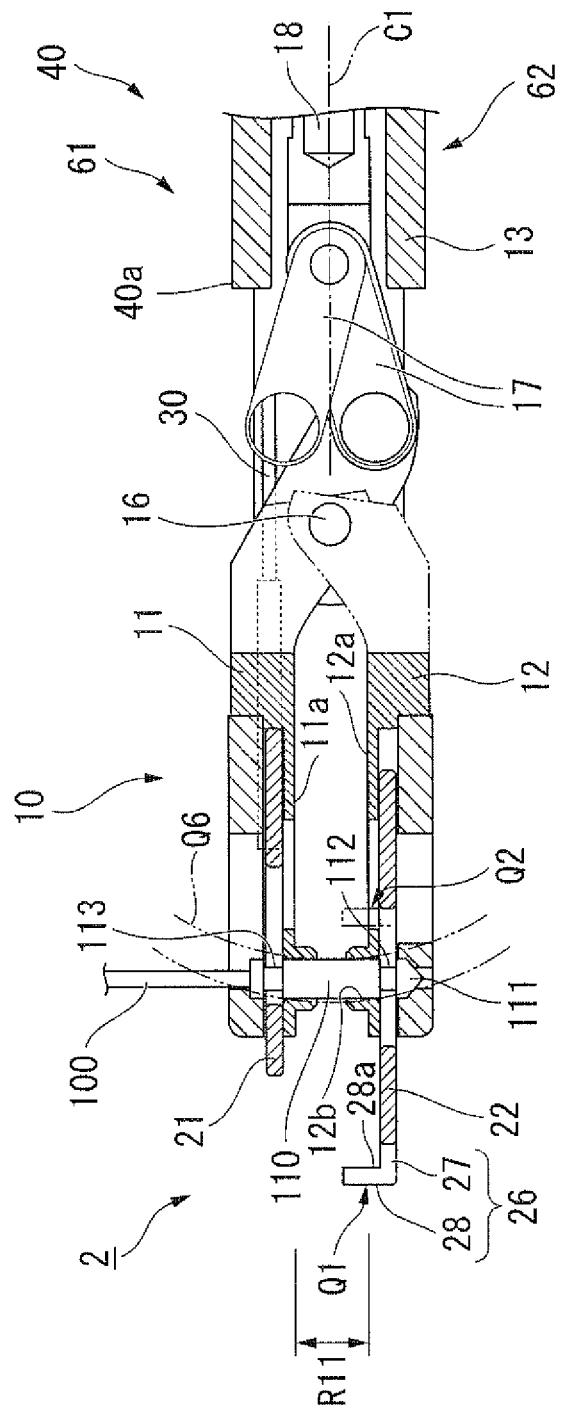
FIG. 7 is a sectional view illustrating dimensions of a part in FIG. 4.
Figure 8:
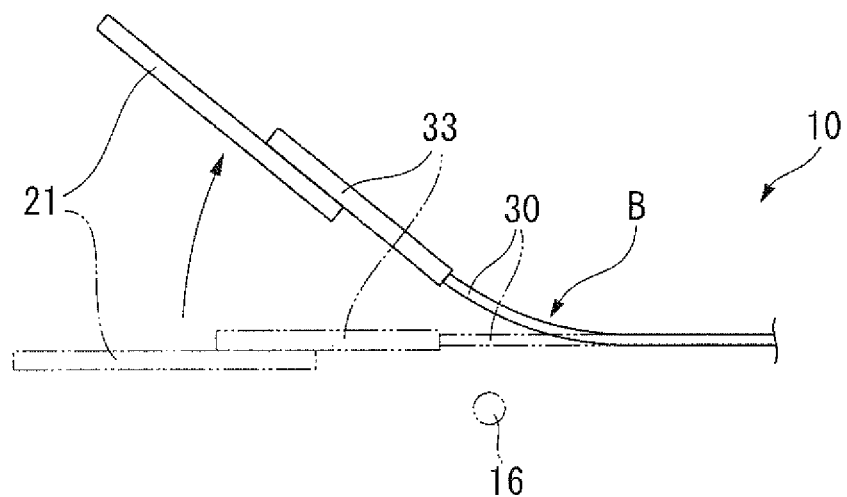
FIG. 8 is an explanatory view for describing an operation of the treatment section in the first embodiment of the present invention.

When the hook 26 moves to the most distal side relative to the second grasping member 12, as illustrated in FIG. 7, the engage portion 28 is disposed at a distal side position Q1 where is located at a distal side with respect to the hollow 12b. The distal side position Q1 of the engage portion 28 is positioned at a distal side relative to the grasping members 11 and 12. On the other hand, when the hook 26 moves to the most proximal side relative to the second grasping member 12, the engage portion 28 is disposed at a proximal side position Q2 where is located at a proximal side with respect to the hollow 12b.

In this way, the engage portion 28 can be moved between the distal side position Q1 and the proximal side position Q2.

Figure 10:
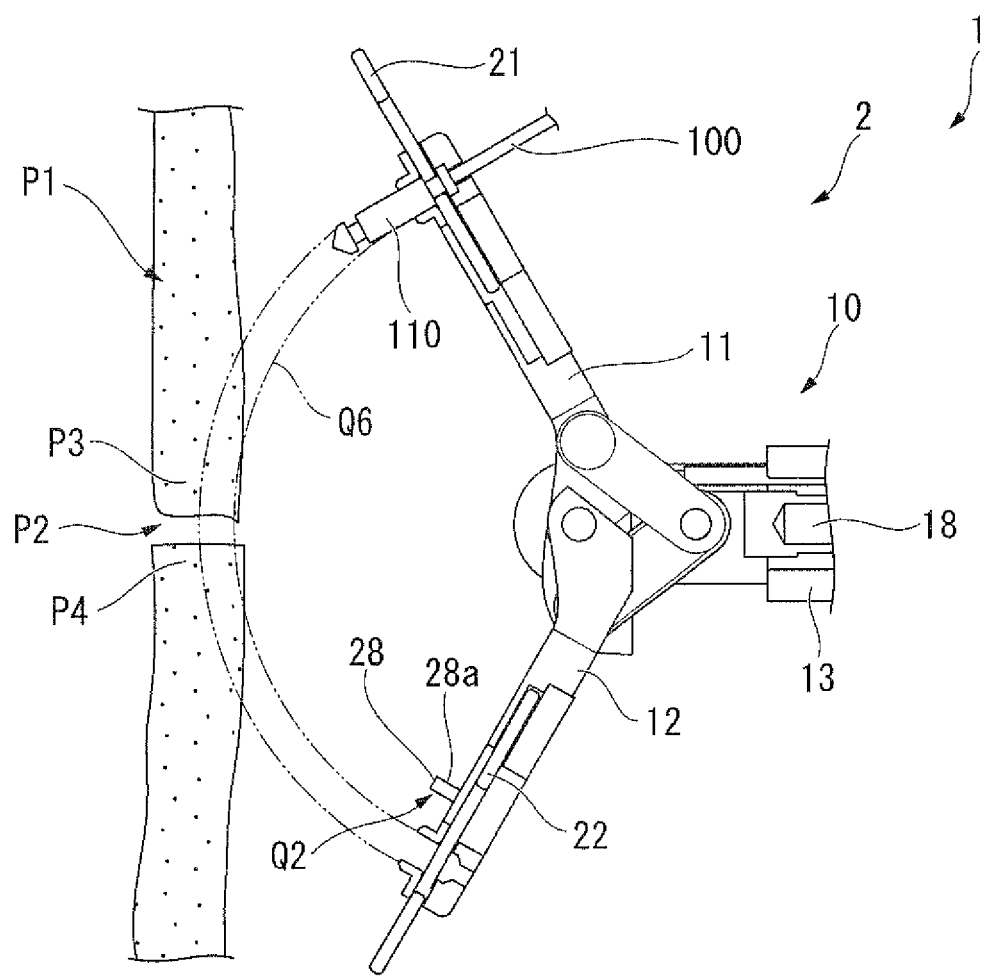
FIG. 10 is a view for describing a procedure using the suture system in the first embodiment of the present invention.

As will be described below, the suture needle 110 is delivered between the grasping members 11 and 12 by a delivery mechanism 62. A track Q6 of the delivered suture needle 110 is illustrated in FIGS. 7 and 10. The engage portion 28 can be moved to the distal side or the proximal side to intersect the track Q6 of the suture needle 110.

FIG. 7 is a side view illustrating a state in which the suture needle 110 is attached to one of the grasping members 11 and 12 and the grasping members 11 and 12 are completely closed. In the state illustrated in FIG. 7, at least a part of the engaging-surface 28a may be within a range R11 between the opposed surface 11a and the opposed surface 12a.

As illustrated in FIG. 6, a distal end of a first delivering wire 30 is fixed to the proximal end of the first needle-fixing member 21. On the other hand, as illustrated in FIG. 3, a distal end of a second delivering wire 31 is fixed to the proximal end of the second needle-fixing member 22. The delivering wires 30 and 31 are disposed at positions away from the links 17 to avoid the links 17.

In the delivering wires 30 and 31, ranges from the pin 16, which connects the grasping members 11 and 12 to act as an opening-closing shaft in the grasping members 11 and 12, to the distal ends of the delivering wires 30 and 31 are covered by hard pipes 33, respectively. Thereby, portions B (see FIGS. 3, 6, and 8) of the delivering wires 30 and 31 which are curved by the opening and closing movements of the grasping members 11 and 12 have flexibility, and portions located at the distal side relative to the curved portions B have high rigidity resistant to buckling.

As illustrated in FIG. 3, the cover member 13 is a tubular member fixed to the distal portion of the longitudinal member 40. The cover member 13 holds both ends of the pin 16. As illustrated in FIG. 4, the links 17 and the opening-closing wire 18 are inserted into the cover member 13. The links 17 and the opening-closing wire 18 are configured to open and close the grasping members 11 and 12. Slits 13a for preventing the grasping members 11 and 12 and the links 17 from interfering with the cover member 13 when the grasping members 11 and 12 are opened and closed is formed in an outer circumferential surface of the cover member 13.

Figure 9:
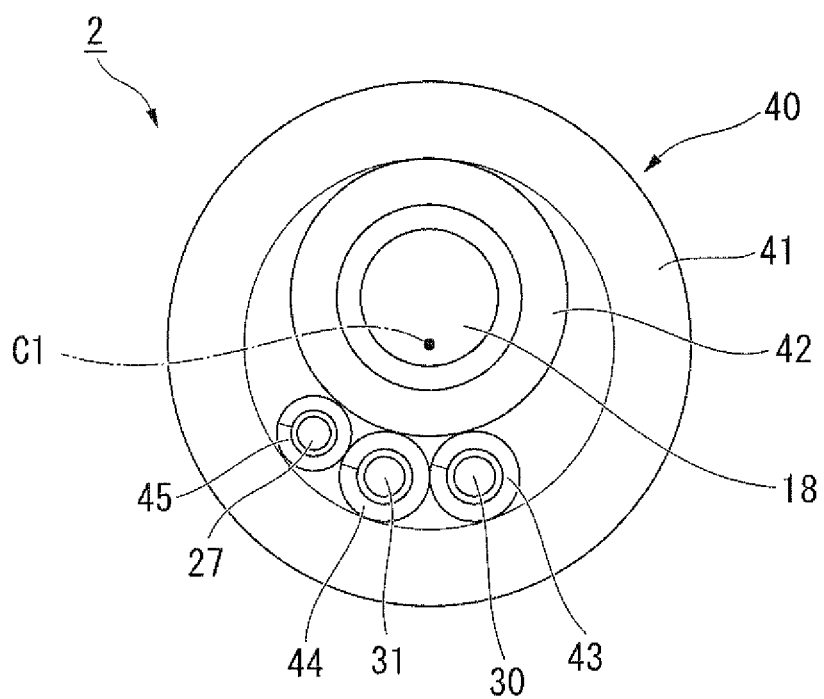
FIG. 9 is a sectional view according to a plane perpendicular to a longitudinal axis of a longitudinal member.

As illustrated in FIG. 9, the longitudinal member 40 has an outer sheath 41 formed of a resin, and a coil sheath 42 inserted into the outer sheath 41. The outer sheath 41 and the coil sheath 42 are flexible members and are elongated along longitudinal axes.

The outer sheath 41 is a tubular member having an outer diameter that can be inserted into a first channel 201 of the endoscope 200 (see FIG. 1). An outer surface of the outer sheath 41 has a surface condition in which frictional resistance to an inner surface of the first channel 201 is low.

The coil sheath 42 is a sheath in which a wire is wound around an axis parallel to the longitudinal axis C1 of the longitudinal member 40 in a coil shape. The coil sheath 42 is a sheath in which a balance between flexibility and resistance to compression applied toward the longitudinal axis C1 is maintained. The opening-closing wire 18 is inserted in the coil sheath 42.

As illustrated in FIG. 9, the outer sheath 41 and the coil sheath 42 are provided in a state in which central lines thereof are offset in parallel. Further, in the present embodiment, second coil sheaths 43 and 44 and a third coil sheath 45 are disposed between the outer sheath 41 and the coil sheath 42. The second coil sheaths 43 and 44 are tubular members into which the delivering wires 30 and 31 are inserted. The third coil sheath 45 is a tubular member into which the rod-like member 27 is inserted. The second coil sheaths 43 and 44 and the third coil sheath 45 are disposed adjacent to each other inside the longitudinal member 40.

As illustrated in FIG. 1, the manipulation section 50 has a first slider 51, second sliders 52 and 53, and a third slider 54. The first slider 51 is provided to push or pull the opening-closing wire 18 that is slidably provided for the manipulation section body 55. The second sliders 52 and 53 are provided to pull the respective delivering wires 30 and 31. The third slider 54 is provided to push or pull the rod-like member 27.

The proximal end of the opening-closing wire 18 is fixed to the first slider 51. The second slider 52 is a slider for pulling the first delivering wire 30. The second slider 53 is a slider for pulling the second delivering wire 31. Proximal ends of the delivering wires 30 and 31 are fixed to the respective second sliders 52 and 53. A proximal end of the rod-like member 27 is fixed to the third slider 54.

As the first slider 51 is moved to the distal side (pushed) relative to the manipulation section body 55, the grasping members 11 and 12 are rotated about the central axis of the pin 16, and the distal portions of the grasping members 11 and 12 are opened.

As the first slider 51 is moved to the proximal side (pulled back) relative to the manipulation section body 55, the grasping members 11 and 12 are rotated, and the distal portions of the grasping members 11 and 12 are closed. That is, as the first slider 51 is manipulated, the grasping members 11 and 12 are opened and closed. The links 17, the opening-closing wire 18, and the first slider 51 constitute an opening-closing mechanism 61 (see FIG. 4) for opening and closing the grasping members 11 and 12.

The hollows 11b and 12b, the needle-fixing members 21 and 22, the delivering wires 30 and 31, and the second sliders 52 and 53 constitute the delivery mechanism 62. The delivery mechanism 62 is provided to deliver the suture needle 110 between the first grasping member 11 and the second grasping member 12.

Although not illustrated, a slit formed in the manipulation section body 55 and a rib formed for the third slider 54 are engaged. Due to this engagement, as described above, the range within which the engage portion 28 can be moved is restricted between the distal side position Q1 and the proximal side position Q2.

The endoscope 200 has a known constitution in which, as illustrated in FIG. 1, a manipulation section 220 is mounted on a proximal portion of a long inserting section 210. A curving section 211 which can be curved is provided at a distal side of the inserting section 210, and a flexible tube portion 212 having flexibility is connected to a proximal side of the curving section 211. The curving section 211 is configured to be able to be manipulated at a knob 221 provided for the manipulation section 220, for instance, by a curving wire (not shown).

A second channel 202 may be formed in the inserting section 210 of the endoscope 200 in parallel with the first channel 201. Distal sides of the channels 201 and 202 may open to a distal surface of the inserting section 210.

Next, a procedure using the suture system 1 of the present embodiment will be described. Hereinafter, a case in which an opening formed in target tissue will be described.

The suture device 2 of the suture system 1 is prepared in a state in which the second slider 52 is pushed into the distal side to attach the suture needle 110 to the first grasping member 11 (this may be paraphrased hereinafter as "pushed"), and the first slider 51 is pulled back to the proximal side to close the grasping members 11 and 12 (this may be paraphrased hereinafter as "pulled back"). At this state, the second slider 53 is pulled back, and the third slider 54 is pulled back to dispose the engage portion 28 at the proximal side position Q2.

Although not illustrated, a body wall of a patient is incised to form an opening, and the inserting section 210 of the endoscope 200 is introduced into a body cavity via the opening. If necessary, the inserting section 210 is introduced while the knob 221 is manipulated to curve the curving section 211, and is held with a distal end thereof facing an opening of target tissue.

The suture device 2 is inserted from the side of the treatment section 10 into the first channel 201 of the endoscope 200, and projects the treatment section 10 from the distal end of the inserting section 210.

As illustrated in FIG. 10, the first slider 51 is pushed to open the grasping members 11 and 12. The suture device 2 is pushed with respect to the endoscope 200, and brings the grasping members 11 and 12 into contact with first and second edges P3 and P4 across the opening P2 of the target tissue P1.

Figure 11:
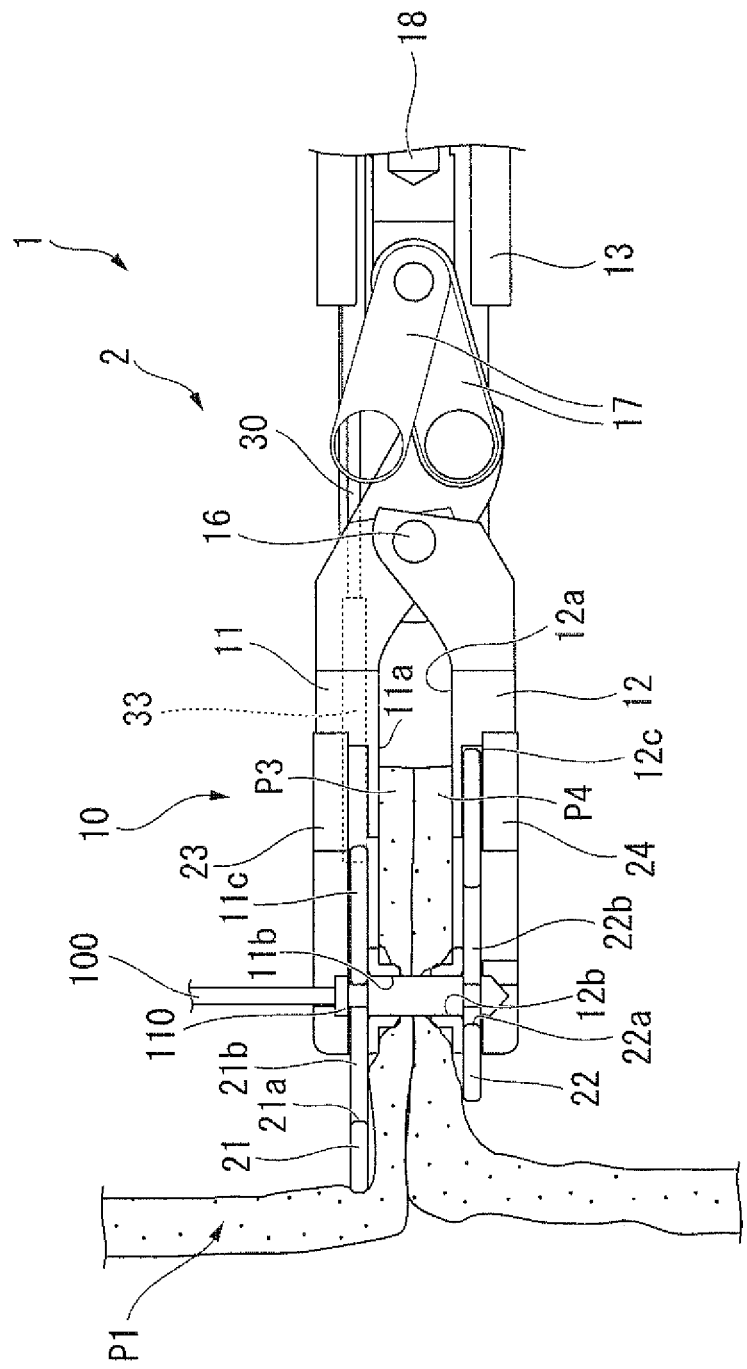
FIG. 11 is a view for describing a procedure using the suture system in the first embodiment of the present invention.

When the first slider 51 is pulled back, the grasping members 11 and 12 are closed as illustrated in FIG. 11. The suture needle 110 attached to the first grasping member 1 enters the hollow 12b of the second grasping member 12. Thereby, the suture needle 110 punctures the edges P3 and P4 between the opposed surfaces 11a and 11b that are disposed to face each other in the grasping members 11 and 12.

If necessary, the first slider 51 is pushed to open the grasping members 11 and 12 with the suture needle 110 attached to the first grasping member 11. Thereby, the suture needle 110 can puncture the edges P3 and P4 again.

In a state in which the grasping members 11 and 12 are closed and the edges P3 and P4 of the target tissue P1 are punctured, the second slider 53 is pushed to attach the suture needle 110 to the second grasping member 12, and the second slider 52 is pulled back to remove the suture needle 110 from the first grasping member 11.

In this state, when the first slider 51 is pushed to open the grasping members 11 and 12, the suture needle 110 moves in a state of being attached to the second grasping member 12, passes through the edges P3 and P4, and is pulled out. As a result, the suture thread 100 fixed to the suture needle 110 is inserted into the edges P3 and P4.

Figure 12:
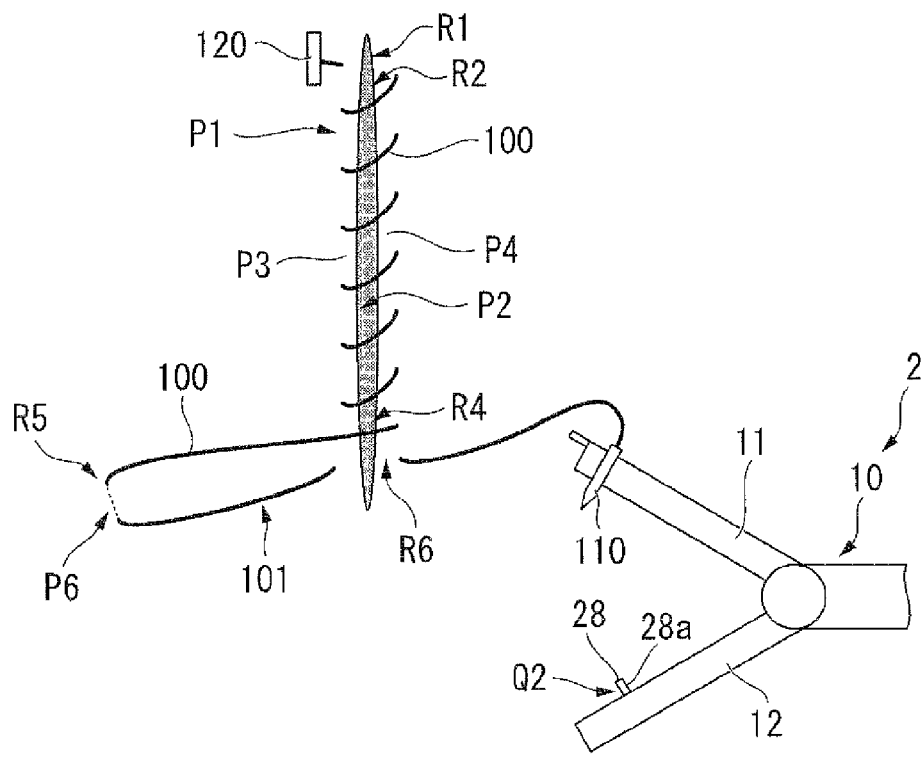
FIG. 12 is a schematic view for describing a procedure using the suture system in the first embodiment of the present invention.

Due to a manipulation of manipulating the knob 221 of the endoscope 200 to curve the curving section 211, as illustrated in FIG. 12, the suture needle 110 is kept away from a position R1 that is a portion at which the suture thread 100 is inserted into the edges P3 and P4. As the suture thread 100 is pulled, the suture thread 100 inserted into the edges P3 and P4 is moved, and the T-bar 120 is caught on the edge P3. At this time, as the suture thread 100 is pulled, a tensile force is applied to the suture thread 100.

The opened grasping members 11 and 12 are brought into contact with the edges P3 and P4 at a position R2 shifted from the position R1 along the opening P2.

When the first slider 51 is pulled back, the grasping members 11 and 12 are closed, and the suture needle 110 attached to the second grasping member 12 enters the hollow 11b of the first grasping member 11. Thereby, the suture needle 110 punctures the edges P3 and P4 between the grasping members 11 and 12.

The second slider 52 is pushed to attach the suture needle 110 to the first grasping member 11, and the second slider 53 is pulled back to remove the suture needle 110 from the second grasping member 12. In this state, when the first slider 51 is pushed to open the grasping members 11 and 12, the suture needle 110 moves in a state of being attached to the first grasping member 11, passes through the edges P3 and P4, and is pulled out. As a result, the suture thread 100 fixed to the suture needle 110 is inserted into the edges P3 and P4. A tensile force is applied to the suture thread 100 by pulling the suture thread 100.

In this way, while the suture needle 110 is delivered between the grasping members 11 and 12 by the delivery mechanism 62, the edges P3 and P4 are repeatedly sewn along the opening P2 of the target tissue P1. At this time, the suture needle 110 delivered between the grasping members 11 and 12 moves along the track Q6 as illustrated in FIG. 7.

The target tissue P1 is sewn along the opening P2 throughout nearly the full length of the opening P2, and is sewn at a position R4 illustrated in FIG. 12. Then, tissue P6 is sewn once at a position R5 separated from the opening P2 by a predetermined distance. The edges P3 and P4 are sewn at a position R6 shifted from the position R4 along the opening P2 again.

Thereby, two suture threads 100 (hereinafter referred to as "thread guard portion 101") are disposed nearly in parallel between the position R4 and the position R5 and between the position R5 and the position R6. A tensile force is also applied to the suture threads 100 of the thread guard portion 101.

Subsequently, the suture thread 100 is entangled in the thread guard portion 101, and a surgical knot that is a known knot is formed at the suture thread 100.

First, in a state in which the grasping members 11 and 12 are opened, the third slider 54 is pushed to move the rod-like member 27 to the distal side, and disposes the engage portion 28 at the distal side position Q1. The engage portion 28 is passed between the thread guard portion 101 and its surrounding tissue P6, and the thread guard portion 101 is caught on the engaging-surface 28a of the engage portion 28. The engage portion 28 disposed at the distal side position Q1 is disposed at the distal side relative to the grasping members 11 and 12. For this reason, the thread guard portion 101 can be easily caught on the engaging-surface 28a of the engage portion 28 without being interfered by the grasping members 11 and 12.

Figure 13:
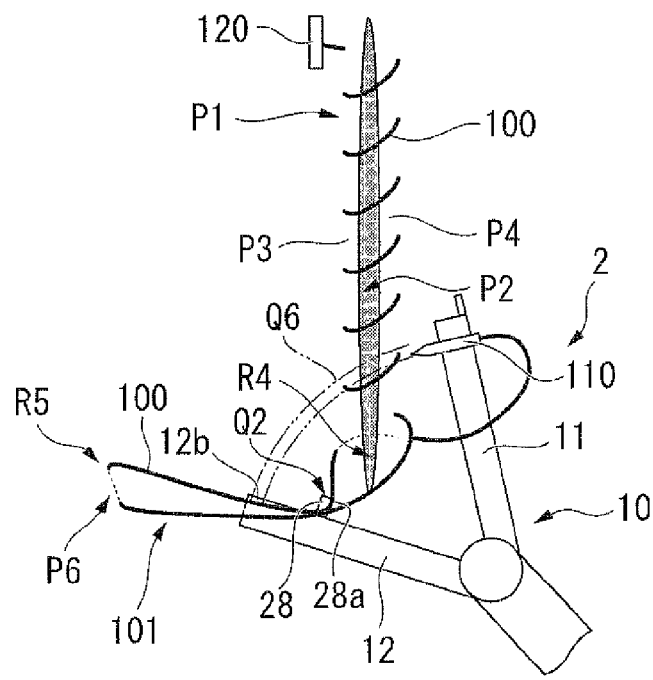
FIG. 13 is a schematic view for describing a procedure using the suture system in the first embodiment of the present invention.

As illustrated in FIG. 13, the third slider 54 is pulled back to dispose the engage portion 28 at the proximal side position Q2. A portion of the thread guard portion 101, which is caught on the engaging-surface 28a, moves to the proximal side relative to the hollow 12b.

The thread guard portion 101 loosens between the position R4 and the position R5 and between the position R5 and the position R6. That is, each of the suture threads 100 constituting the thread guard portion 101 is longer than a distance between the position R4 and the position R5 and a distance between the position R5 and the position R6.

Figure 14:
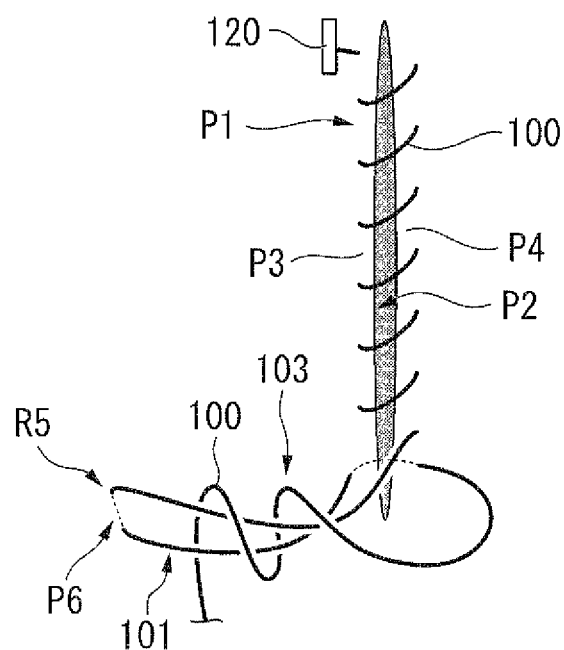
FIG. 14 is a schematic view for describing a procedure using the suture system in the first embodiment of the present invention.
Figure 15:
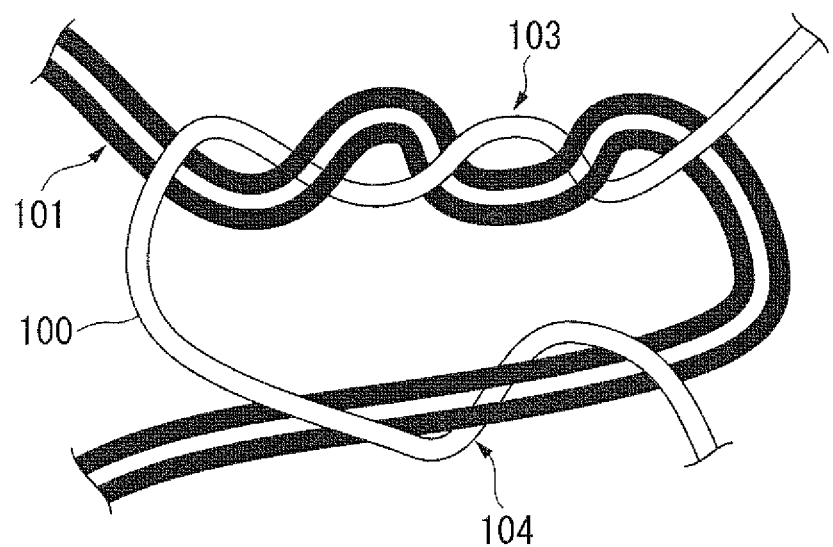
FIG. 15 is a view for describing a surgical knot used in a procedure using the suture system in the first embodiment of the present invention.

The distal portions of the grasping members 11 and 12 are closed, and the suture needle 110 is delivered between the grasping members 11 and 12. Thereby, as illustrated in FIGS. 14 and 15, the suture thread 100 is wound twice around the thread guard portion 101 in one direction, and a first ligation portion 103 is formed by the thread guard portion 101 and the suture thread 100. In FIG. 15, the suture threads 100 constituting the thread guard portion 101 are indicated in black. When the engage portion 28 is disposed at the proximal side position Q2, a portion of the thread guard portion 101, which is caught on the engaging-surface 28a, moves to the proximal side relative to the hollow 12b. Thus, as the distal portions of the grasping members 11 and 12 are closed, the suture thread 100 can be easily wound around the thread guard portion 101.

As illustrated in FIG. 15, the suture thread 100 is wound once around the thread guard portion 101 in a direction opposite to the winding direction of the first ligation portion 103. Thereby, a second ligation portion 104 is formed by the thread guard portion 101 and the suture thread 100.

Afterwards, due to the manipulation of manipulating the knob 221 to curve the curving section 211, the first ligation portion 103 and the second ligation portion 104 are constricted to form a surgical knot. Thereby, a state in which the opening P2 of the target tissue P1 is sutured by the suture thread 100 is held.

The suture thread 100 located at the proximal side relative to the portion of the suture thread 100 at which the surgical knot is formed is cut by, for instance, scissors (not shown) inserted from the second channel 202.

The suture device 2 is pulled back and ejected from the endoscope 200, and the endoscope 200 is ejected from the body cavity of the patient. When the suture needle 110 is removed from the first grasping member 11 outside of the body of the patient, the suture thread 100 is removed through the slit 21c of the first needle-fixing member 21. A suitable treatment is performed on the patient, and a series of procedures is completed.

According to the suture device 2 of the present embodiment, the engage portion 28 can be moved between the distal side position Q1 located at the distal side relative to the hollow 12b of the second grasping member 12 and the proximal side position Q2 located at the proximal side relative to the hollow 12b by the delivery mechanism 62.

In the state in which the distal portions of the grasping members 11 and 12 are opened, the thread guard portion 101 is caught on the engage portion 28 disposed at the distal side position Q1, and the engage portion 28 is moved to the proximal side position Q2. The portion of the thread guard portion 101 which is caught on the engage portion 28 moves to the proximal side relative to the hollow 12b.

The grasping members 11 and 12 are closed by the opening-closing mechanism 61, and the suture needle 110 is delivered between the grasping members 11 and 12 by the delivery mechanism 62. Thereby, the suture thread 100 can be easily wound around the thread guard portion 101. Accordingly, the suture device 2 according to the present embodiment can form a surgical knot at the suture thread 100 without using a separate surgical instrument, and hold the state in which the opening P2 of the target tissue P1 is sutured.

One opening for introducing the inserting section 210 of the endoscope 200, i.e. the suture device 2, is only formed in the body wall of the patient, and thereby the suture device 2 according to the present embodiment can form the knot at the suture thread 100.

The distal side position Q1 of the engage portion 28 is located at the distal side relative to the grasping members 11 and 12. For this reason, when the thread guard portion 101 is caught on the catch portion 28, the thread guard portion 101 can be easily caught on the engage portion 28 without being interfered by the grasping members 11 and 12.

Since the rod-like member 27 is connected to the engage portion 28, the engage portion 28 can be easily moved between the distal side position Q1 and the proximal side position Q2 by advancing or retreating the rod-like member 27. If the hook 26 is formed by bending the wire, the hook 26 can be formed with ease and at a suppressed production cost.

In the present embodiment, a constitution in which the distal side position Q1 of the engage portion 28 is located at the distal side relative to the grasping members 11 and 12 is shown. However, the distal side position of the engage portion 28 may be the same position as the distal ends of the grasping members 11 and 12. This is because, even if the range within which the engage portion 28 moves at the distal side is set in this way, the thread guard portion 101 can be caught on the engage portion 28 disposed at the distal side position.

Figure 16:
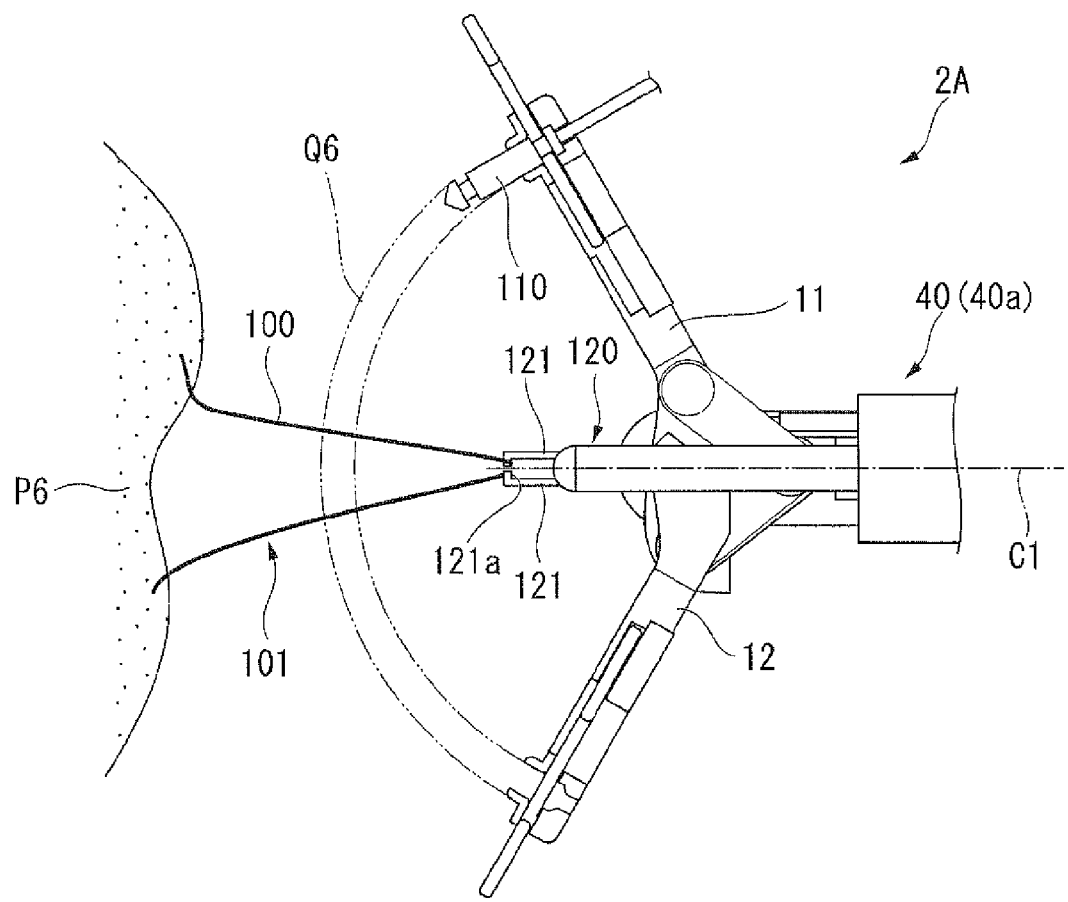
FIG. 16 is a side view of a distal portion of a suture device in a modified example of the first embodiment of the present invention.

A distal portion of a suture device 2A in a modified example of the first embodiment of the present invention is illustrated in FIG. 16. Like the suture device 2A illustrated in FIG. 16, a grasping instrument 120 may be configured to be inserted into a longitudinal member 40 to enable advancing or retreating manipulation. The suture device 2A of the present modified example has a pair of grasping pieces 121. The pair of grasping pieces 121 are provided for a distal portion 40a of the longitudinal member 40, and can be opened and closed. Distal portions of the pair of grasping pieces 121 become engage portions 121a. Even with this constitution, by advancing or retreating the grasping instrument 120 relative to the longitudinal member 40, the engage portions 121a can be moved between a distal side position located at a distal side relative to a suture needle 110 attached to a second grasping member 12 and a proximal side position located at a proximal side relative to the suture needle 110, that is, to intersect a track Q6 of the suture needle 110.

In the present embodiment, a constitution in which the hook 26 is provided for the second grasping member 12 is shown. The hook may be provided for the first grasping member 11 or the longitudinal member 40.

In the present embodiment, the opposed surfaces 11a and 12a of the grasping members 11 and 12 may function as grasping surfaces that actually grasp the tissue when the tissue is grasped by the treatment section 10.

Second Embodiment

Next, a second embodiment of the present invention will be described with reference to FIGS. 17 to 20. The same parts as in the first embodiment are given the same symbols and detailed description thereof will be omitted, describing only different points.

Figure 17:
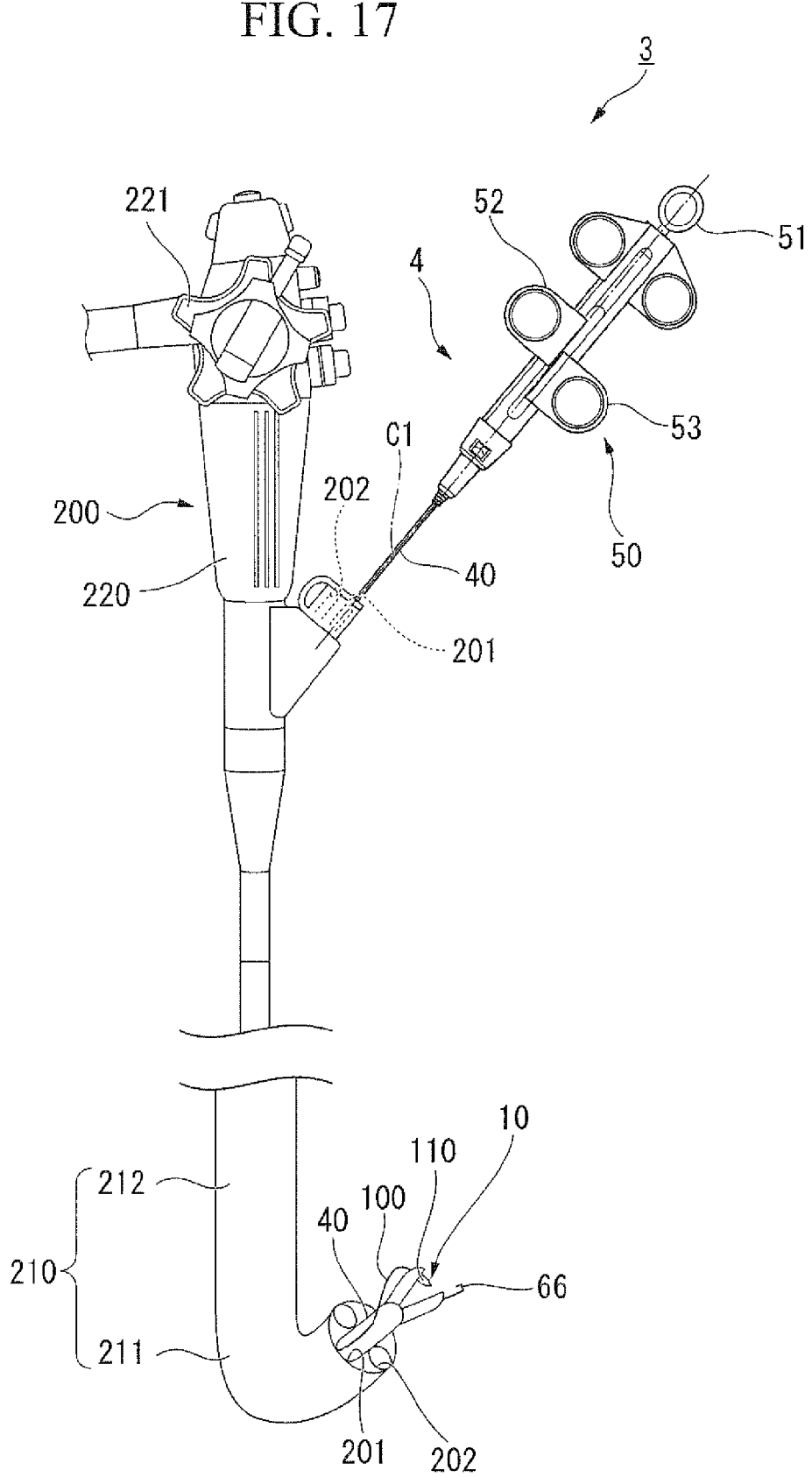
FIG. 17 is an overall view of a suture system provided with a suture device according to a second embodiment of the present invention.
Figure 18:
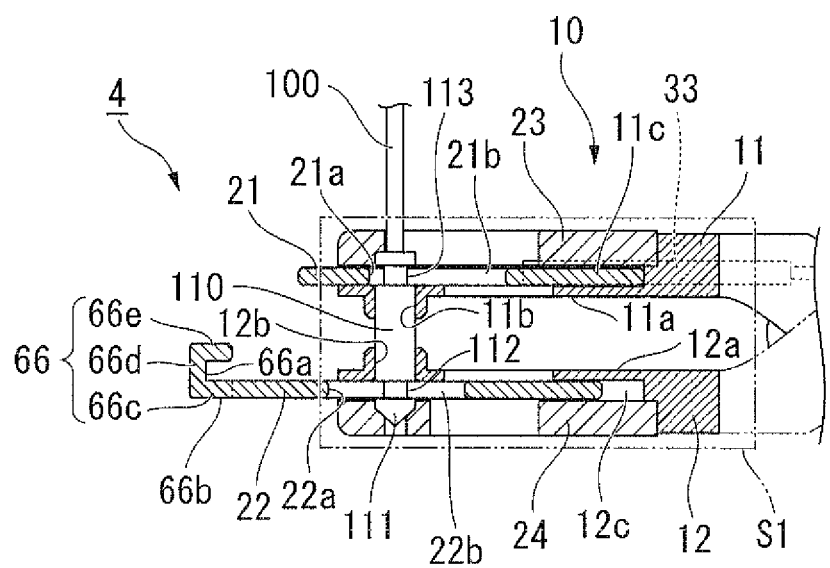
FIG. 18 is a side sectional view of a distal portion of the suture device according to the second embodiment of the present invention.

As illustrated in FIGS. 17 and 18, a suture device 4 according to the present embodiment is used along with the aforementioned endoscope 200. The suture device 4 and the endoscope 200 constitute a suture system 3.

In place of the support member 25, the hook 26, and the third slider 54 of the suture device 2 according to the first embodiment, the suture device 4 has an engage portion 66 provided at a second needle-fixing member 22.

Figure 19:
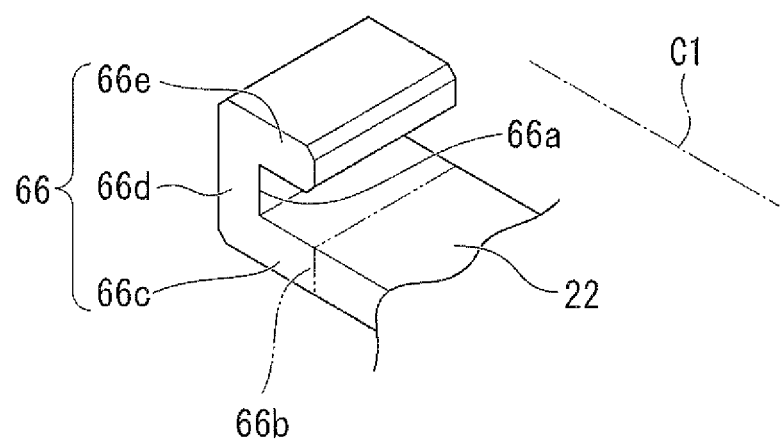
FIG. 19 is a perspective view of an engage portion provided for a treatment section of the suture device according to the second embodiment of the present invention.

As illustrated in FIGS. 18 and 19, a groove portion 66a is formed at the engage portion 66. The groove portion 66a is open on a proximal side, and passes through the engage portion 66 in a direction perpendicular to a longitudinal axis C1. The groove portion 66a extends in a direction perpendicular to a reference plane S1 on which grasping members 11 and 12 are opened and closed. That is, the engage portion 66 has a base portion 66c, a protrusion portion 66d, and a return portion 66e. The base portion 66c has a proximal portion joined to a distal end of the second needle-fixing member 22, and extends forward along the second needle-fixing member 22. The protrusion portion 66d is provided to stand in a direction protruding from a distal end of the base portion 66c toward the first grasping member 11. The return portion 66e runs in a direction returning to the proximal side from a distal end of the protrusion portion 66d in the protruding direction. The aforementioned groove portion 66a is defined by the base portion 66c, the protrusion portion 66d, and the return portion 66e. A distance between the base portion 66c and the return portion 66e is equal to or greater than an outer diameter of a suture thread 100. The protrusion portion 66d and the return portion 66e are disposed at the side of the first grasping member 11 for the second needle-fixing member 22. That is, the engage portion 66 is formed to be curved toward the first grasping member 11. The engage portion 66 is formed of a material such as stainless steel having elasticity integrally with the second needle-fixing member 22. The second needle-fixing member 22 functions to support the groove portion 66a.

In the present embodiment, the engage portion 66 is provided at a distal portion of the second grasping member 12 to protrude forward from the second grasping member 12. The groove portion 66a is open on the proximal side when the grasping members 11 and 12 are closed.

Next, a procedure using the suture system 3 of the present embodiment will be described.

The suture device 4 is prepared in a state in which the grasping members 11 and 12 are closed.

Since the protrusion portion 66d and return portion 66e of the engage portion 66 are disposed at the side of the first grasping member 11 for the second needle-fixing member 22, when the engage portion 66 is inserted into a first channel 201 of the endoscope 200, it is difficult for the engage portion 66 to come into contact with an inner surface of the first channel 201.

After edges P3 and P4 are sewn along an opening P2, a thread guard portion 101 is formed by suture threads 100.

Figure 20:
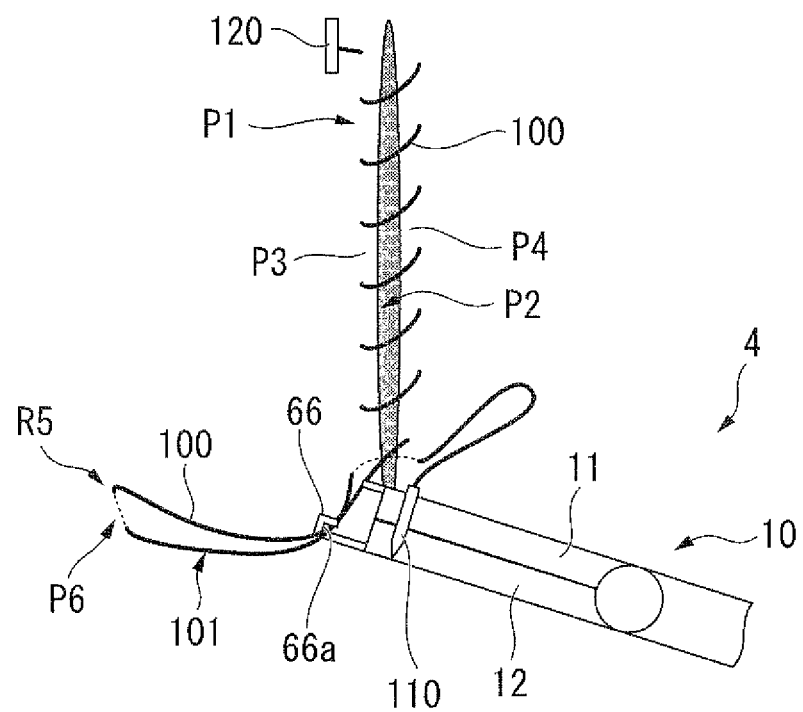
FIG. 20 is a schematic view for describing a procedure using the suture system in the second embodiment of the present invention.

The first slider 51 is pulled back to close the grasping members 11 and 12 as illustrated in FIG. 20. The thread guard portion 101 is hung on the groove portion 66a of the engage portion 66 of the suture device 4. The engage portion 66 is provided at the distal portion of the second grasping member 12 to protrude forward from the second grasping member 12. For this reason, the grasping members 11 and 12 hardly disturb the thread guard portion 101 when the thread guard portion 101 is hung on the groove portion 66a.

Next, the suture device 4 is pulled back to loosen the thread guard portion 101. When the grasping members 11 and 12 are closed, the groove portion 66a is open on the proximal side. For this reason, when the suture device 4 is pulled back in the state in which the grasping members 11 and 12 are closed, the thread guard portion 101 is hardly released from the groove portion 66a.

Subsequently, as described above, the suture thread 100 is entangled in the thread guard portion 101, and a surgical knot of the suture thread 100 is formed. Since the thread guard portion 101 loosens, the suture needle 110 or the suture thread 100 can easily pass between the thread guard portion 101 and tissue P6.

As described above, according to the suture device 4 of the present embodiment, the thread guard portion 101 can be loosened by hanging the thread guard portion 101 on the groove portion 66a of the engage portion 66 and being pulled back the suture device 4. For this reason, it is possible to form a surgical knot at the suture thread 100 by passing the suture thread 100 between the thread guard portion 101 and its surrounding tissue P6 and winding the suture thread 100 around the thread guard portion 101. Therefore, it is possible to form a surgical knot at the suture thread 100 without using a separate surgical instrument.

The engage portion 66 is provided at the distal portion of the second grasping member 12 to protrude forward from the second grasping member 12. For this reason, since the grasping members 11 and 12 hardly disturb two suture threads 100, when two suture threads 100 are hung on the groove portion 66a, it is possible to easily hang the suture threads 100 on the groove portion 66a.

A portion 66b of the groove portion 66a which is located at the side of the second grasping member 12 is joined to the second needle-fixing member 22. For this reason, the return portion 66e or the protrusion portion 66d that is a portion of the groove portion 66a and is located at the side of the first grasping member 11 is disposed at the side of the first grasping member 11 for the second needle-fixing member 22. Thereby, when the suture device 4 is inserted into the first channel 201, the engage portion 66 can be prevented from coming into contact with the inner surface of the first channel 201 to damage the first channel 201.

When the grasping members 11 and 12 are closed, the groove portion 66a is open on the proximal side. Therefore, when the suture device 4 is pulled back in the state in which the grasping members 11 and 12 are closed, the suture thread 100 is possible to prevent from being released from the groove portion 66a.

Third Embodiment

Next, a third embodiment of the present invention will be described with reference to FIGS. 21 and 22. The same parts as in the first and second embodiments are given the same symbols and detailed description thereof will be omitted, describing only different points.

Figure 21:
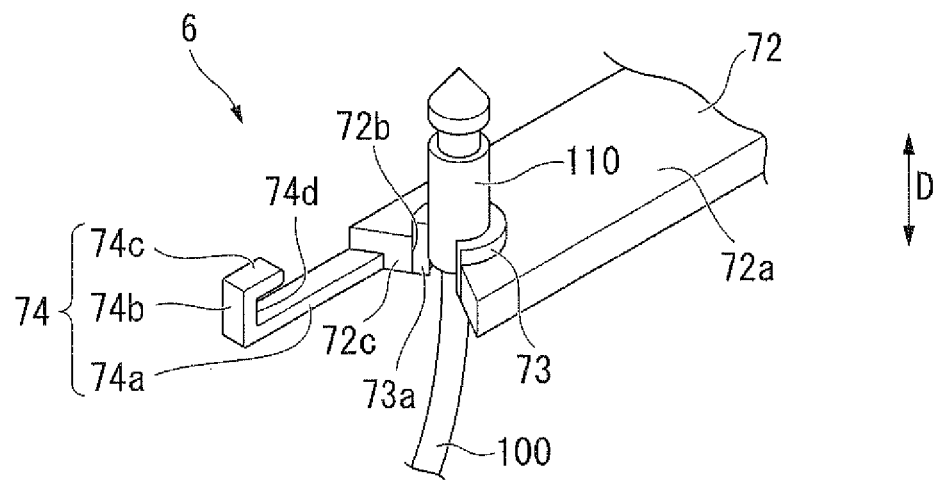
FIG. 21 is a perspective view of major parts in a suture device according to a third embodiment of the present invention.

As illustrated in FIG. 21, a through-hole 72b is formed at a second grasping member 72 of a suture device 6 according to the present embodiment. The through-hole 72b extends in a thickness direction D that is a direction away from the opposed surface 72a relative to a first grasping member 11 (not shown). A recess portion 72c is formed at the second grasping member 72. The recess portion 72c extends from a distal surface to a proximal side, and passes through the second grasping member 72 in the thickness direction D. The recess portion 72c communicates with the through-hole 72b.

A holding portion 73 is fixed to the through-hole 72b. The holding portion 73 is formed in a tubular shape, allows a suture needle 110 to be held therein, and is fixed in a state in which a central axis of the holding portion 73 is matched in the thickness direction D. A cutout portion 73a is formed at the holding portion 73. The cutout portion 73a passes through the holding portion 73 in a radial direction, and is formed over the full length of the holding portion 73. The holding portion 73 is one of the components of the aforementioned delivery mechanism.

The recess portion 72c of the second grasping member 72 communicates with the cutout portion 73a of the holding portion 73 fixed to the through-hole 72b. The suture thread 100 can be inserted into the recess portion 72c and the cutout portion 73a.

In the present embodiment, the engage portion 74 is directly attached to the second grasping member 72 in such a manner that the cutout portion 73a of the holding portion 73 is avoided in one of width directions of the second grasping member 72. To be more specific, the engage portion 74 has a base portion 74a, a protrusion portion 74b, and a return portion 74c. The base portion 74a is joined to a distal end of the second grasping member 72 at a proximal portion, and extends forward along the second grasping member 72. The protrusion portion 74b is provided to stand in a direction protruding from a distal end of the base portion 74a toward a first grasping member 11. The return portion 74c runs to return to the proximal side from a distal end of the protrusion portion 74b in a protruding direction. The groove portion 74d is defined by the base portion 74a, the protrusion portion 74b, and the return portion 74c. The base portion 74a functions to support the groove portion 74d.

As described above, according to the suture device 6 of the present embodiment, it is possible to form a knot at the suture thread 100 to hold a state in which the tissue is sutured after being repeatedly sutured without using a separate surgical instrument.

In the suture device 6 according to the present embodiment, the recess portion 72c of the second grasping member 72 and the cutout portion 73a of the holding portion 73 are formed. Therefore, by drawing the suture thread 100 forward through the recess portion 72c and the cutout portion 73a, the suture needle 110 fixing the suture thread 100 can be easily removed from the holding portion 73 from the state of attaching the suture needle 110 to the holding portion 73.

Figure 22:
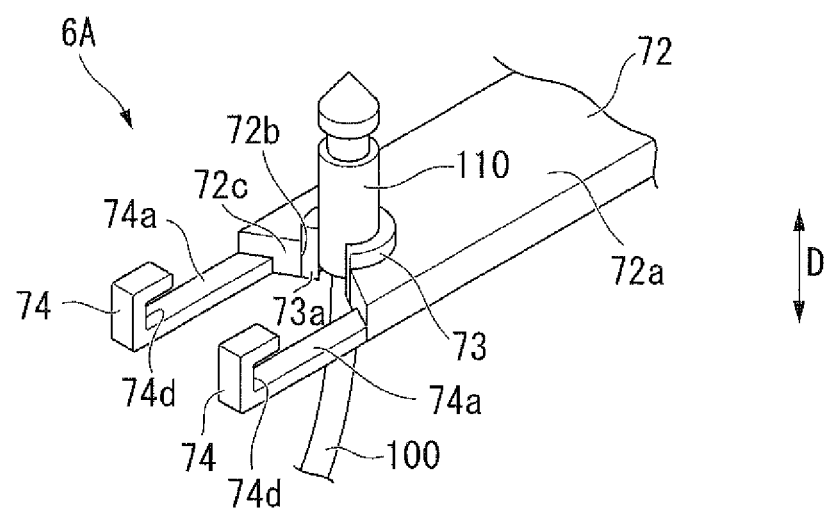
FIG. 22 is a view of major parts in a modified example of the suture device according to the third embodiment of the present invention.

A main parts of a suture device 6A in a modified example of the third embodiment is illustrated in FIG. 22. In the present embodiment, like the suture device 6A illustrated in FIG. 22, a pair of engage portions 74 may be attached to the second grasping member 72 to sandwich the cutout portion 73a of the holding portion 73 in a width direction of the second grasping member 72.

With this constitution, it is possible to easily hang a thread guard portion 101 on the groove portion 74d of the engage portion 74 in any width directions of the second grasping member 72.

Although the first to third embodiments of the present invention have been described in detail with reference to the drawings, the specific constitution is not limited to these embodiments. A change in the constitution is included without departing from the gist of the present invention. Each of the constitutions illustrated in each of the embodiments may be used in an appropriate combination.

For example, in the first to third embodiments, an example in which the distal member is the suture needle 110 is shown. However, any shape is possible as long as the shape of the distal member is a shape in which the tissue can be punctured.

Figure 23:
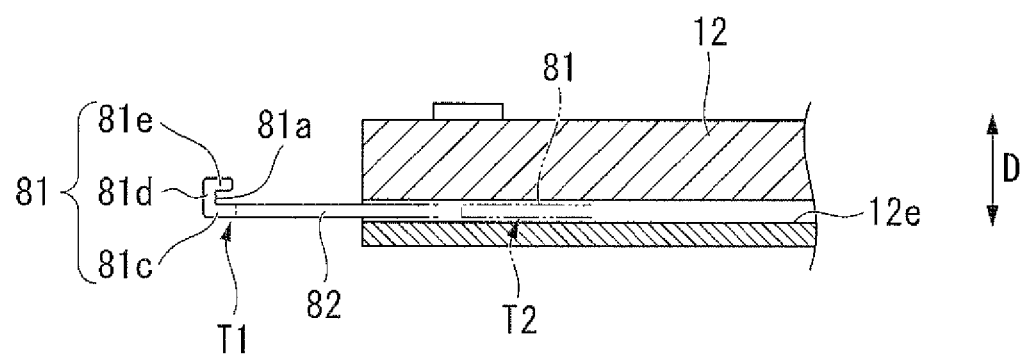
FIG. 23 is a perspective view of the major parts in the modified example of the suture device according to the third embodiment of the present invention.

In the second and third embodiments, as illustrated in FIG. 23, an engage portion 81 provided to protrude forward from the second grasping member 12 may be configured to be housed in a channel 12e formed in the second grasping member 12.

A distal end of a manipulation member 82 formed in a plate shape is joined to a proximal end of a base portion 81c of the engage portion 81. A length of the channel 12e in a thickness direction D is slightly longer than that of the manipulation member 82 or the base portion 81c in the thickness direction D.

The engage portion 81 may be formed of a shape-memory alloy such as nickel titanium having elasticity.

If the manipulating member 82 is moved (pulled back) to a proximal side relative to the second grasping member 12, the engage portion 81 is moved to the proximal side, and is housed in the channel 12e. At this time, as the engage portion 81 is curved, the engage portion 81 is elastically deformed from a normal state T1 in which the groove portion 81a is formed to a housed state T2 in which the base portion 81c, the protrusion portion 81d, and the return portion 81e constituting the engage portion 81 are elongated in a flat shape. On the other hand, if the manipulating member 82 is moved to a distal side relative to the second grasping member 12, when the engage portion 81 is moved to the distal side and protrudes forward from the channel 12e, the engage portion 81 is deformed from the flat housed state T2 to the curved normal state T1 by its elastic force.

In the normal state T1, the engage portion 81 has enough rigidity to resist deformation even if the thread guard portion 101 is hung on the groove portion 81a and is pulled back.

When the thread guard portion 101 loosens, the engage portion 81 is set to the normal state T1, and the thread guard portion 101 is hung on the groove portion 81a and is pulled back. When the target tissue P1 is sewn by the grasping members 11 and 12, the engage portion 81 is set to the housed state T2.

The manipulating member 82 functions to support the groove portion 81a.

With this constitution, when the target tissue P1 is sewn by the grasping members 11 and 12, it is possible to prevent the engage portion 81 from disturbing the grasping members 11 and 12.

Figure 24:
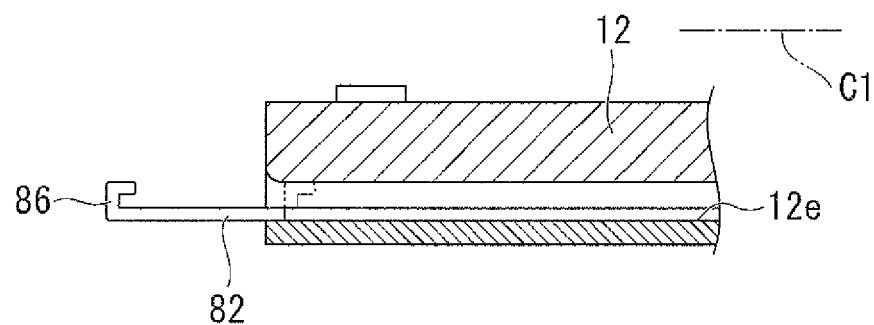
FIG. 24 is a sectional view of the major parts in the modified example of the suture device according to the third embodiment of the present invention.

As illustrated in FIG. 24, an engage portion 86 may be movable along a longitudinal axis C1, and may be configured to be housed in a channel 12e of a second grasping member 12 with the engage portion 86 maintained in a curved shape when a manipulating member 82 is pulled back.

Even with this constitution, when the target tissue P1 is sewn by the grasping members 11 and 12, it is possible to prevent the engage portion 86 from disturbing the grasping members 11 and 12.

In the second and third embodiments, the direction in which the groove portion of the engage portion passes is set to a direction perpendicular to the longitudinal axis C1, but may be set to a direction intersecting the longitudinal axis C1.

Even when the suture device 2 according to the second embodiment is not provided with the return portion 66e, when the suture device 6 or 6A according to the third embodiment is not provided with the return portion 74c, and when the suture device in the aforementioned modified example is not provided with the return portion 81e, the thread guard portion 101 can be loosened. For this reason, in each embodiment and modified example, the return portions 66e, 74c, and 81e may be omitted.

Figure 25:
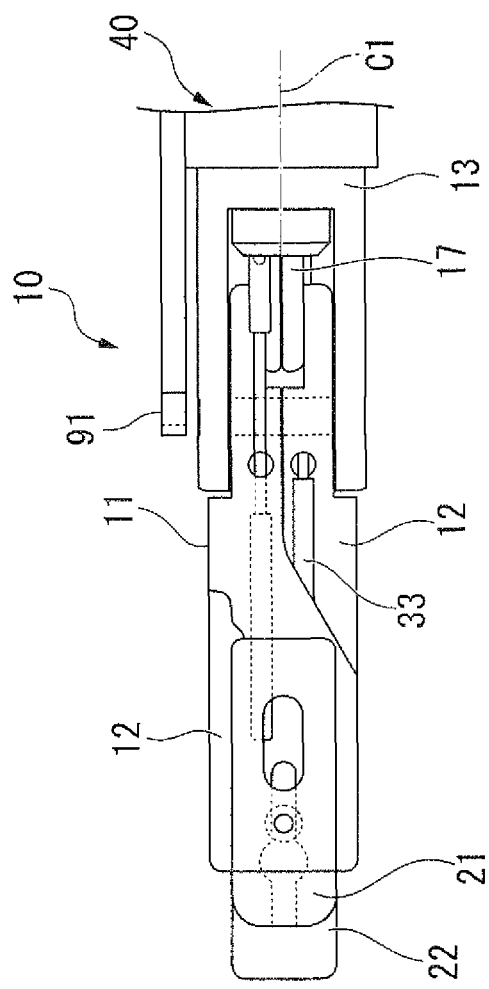
FIG. 25 is a plan view illustrating a part of the modified example of the suture device according to the third embodiment of the present invention.

In the embodiments, an example in which the engage portion is provided at the distal portion of the second grasping member is shown. However, as illustrated in FIG. 25, the engage portion 91 may be provided for a portion other than the grasping member, such as the distal portion 40a of the longitudinal member 40. In the embodiments, the engage portion 91 is disposed at a position at which it does not protrude forward from the second grasping member 12.

A space is provided inside the second grasping member, and the engage portion is housed in the space. Thereby, the engage portion may be configured not to protrude forward from the second grasping member. In this case, when the suture device is inserted into or removed from the human body, the engage portion is housed in the second grasping member. Thus, when the engage portion is engaged with the thread guard portion 101 of the suture thread 100, the engage portion protrudes from the distal end of the second grasping member.

In the embodiments, an example in which the engage portion is formed to be curved toward the first grasping member 11 is shown. However, the engage portion may be formed to be curved toward the opposite side of the first grasping member 11.

In the embodiments, an example in which the groove portion of the engage portion is open on the proximal side when the grasping members 11 and 12 are closed is shown. However, the groove portion may be configured to be open on the proximal side when the grasping members 11 and 12 are opened. Even with this constitution, the suture device is pulled back in the state in which the grasping members 11 and 12 are opened. Thereby, it can be difficult for the thread guard portion 101 to deviate from the groove portion.

In the embodiments, an example in which the engage portion is provided for the second grasping member is shown. However, the engage portion may be provided for both of the first grasping member and the second grasping member.

In the embodiments, an example in which the longitudinal member 40 is the elastic member formed of a flexible member is shown. However, the longitudinal member may be a hard member that does not easily bend.

Although embodiments of the present invention have been described, the technical scope of the present invention is not limited to these embodiments. The combinations of the components in the embodiments can be changed without departing from the gist of the present invention, or each component can be variously modified or removed. The present invention is not limited by the above description, but is only limited by the appended claims.

What is claimed is:

1. A suture device, comprising;
a longitudinal member extended along a longitudinal axis;
a first grasping member and a second grasping member provided at a distal portion of the longitudinal member and configured to enable opening-closing movement, the first grasping member and the second grasping member each being configured to detachably attach to a distal member to which a suture thread is fixed;
a receiving portion which has a hollow positioned at the second grasping member at a proximal side relative to a distal end of the second grasping member, wherein the hollow detachably mounts the distal member so that a part of the distal member protrudes from the second grasping member toward the first grasping member;
a hook supported by the second grasping member so as to be movable between a distal position located at a distal side relative to the distal end of the second grasping member, and a proximal position located at a proximal side relative to the hollow, and which is formed in a hook shape; and
a manipulation section which is provided at a proximal portion of the longitudinal member and is configured to advance or retreat the hook.

2. The suture device according to claim 1, further comprising:
a rod-like member configured to extend along the longitudinal axis and provided at the second grasping member so as to be movable; and
a support member configured to hold the rod-like member to be movable along a longitudinal axis of the second grasping member,
wherein a distal portion of the rod-like member is connected to the hook.

3. The suture device according to claim 1, wherein:
the distal member is a suture needle;
the suture device further comprising a needle-fixing member that is inserted into the second grasping member and configured to fix the suture needle to the second grasping member;
wherein the needle-fixing member has the distal portion protruding from a distal end of the second grasping member; and
the hook is provided at the distal portion of the needle-fixing member.

4. The suture device according to claim 1, wherein:
the first grasping member has a first surface facing the second grasping member;
the second grasping member has a second surface facing the first grasping member; and
an engaging-surface provided at the hook extends in a direction approximately perpendicular to the second surface, and from the second surface toward the first surface.

5. The suture device according to claim 4, wherein the hook is configured to be movable along the longitudinal axis between a distal side and a proximal side relative to the distal member.

6. The suture device according to claim 1, wherein the first grasping member or the second grasping member includes a member that defines a slit that engages a recess formed in an outer circumferential surface of the distal member.

* * * * *